(12) United States Patent
Satoh et al.

(10) Patent No.: US 8,343,348 B2
(45) Date of Patent: Jan. 1, 2013

(54) METHOD FOR PRODUCING CARBON FILM, CARBON FILM AND SEPARATOR

(75) Inventors: Aya Satoh, Nagoya (JP); Nobuhiko Mori, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 13/338,692

(22) Filed: Dec. 28, 2011

(65) Prior Publication Data

US 2012/0091056 A1 Apr. 19, 2012

Related U.S. Application Data

(63) Continuation of application No. PCT/JP2010/059217, filed on May 31, 2010.

(30) Foreign Application Priority Data

Jul. 10, 2009 (JP) ................................. 2009-163634
Nov. 19, 2009 (JP) ................................. 2009-264327

(51) Int. Cl.
*B01D 63/00* (2006.01)
*B01D 15/00* (2006.01)
*B01D 39/00* (2006.01)
*B01D 39/14* (2006.01)
*B29C 33/48* (2006.01)
*B29C 65/00* (2006.01)

(52) U.S. Cl. .................. 210/651; 210/640; 210/500.25; 210/510.1; 210/490; 264/41; 264/45.2; 95/52

(58) Field of Classification Search ............. 210/500.25, 210/500.21, 500.1, 640, 651, 510.1; 264/41, 264/45.5; 95/45, 52

See application file for complete search history.

(56) References Cited

U.S. PATENT DOCUMENTS

| 4,711,719 | A | 12/1987 | Leenaars et al. |
| 5,089,135 | A | 2/1992 | Yoneyama et al. |
| 7,493,897 | B2 | 2/2009 | Arakawa et al. |
| 2008/0302243 | A1 * | 12/2008 | Byrd et al. .......................... 95/278 |
| 2011/0072965 | A1 * | 3/2011 | Lie et al. ............................ 95/47 |

FOREIGN PATENT DOCUMENTS

JP 60-156510 A1 8/1985

(Continued)

OTHER PUBLICATIONS

B. Smitha et al., "*Separation of Organic-Organic Mixtures by Pervaporation—A Review*," Journal of Membrane Science, Science Direct, vol. 41, 2004, pp. 1-21.

(Continued)

*Primary Examiner* — Ana Fortuna
(74) *Attorney, Agent, or Firm* — Burr & Brown

(57) ABSTRACT

A method for producing a carbon membrane of the present invention is a production method where a carbon membrane obtained by subjecting a carbon-containing layer to thermal decomposition in an oxygen inert atmosphere while sending a gas mixture containing an oxidizing gas thereinto is thermally heated. The carbon membrane is subjected to a heating oxidation treatment with controlling the ratio of the flow rate of the gas mixture to the areas of the carbon membrane to 0.5 cm/min. or more to control (temperature $°C.$)$^2$×time (h)/10000, which is the relation between the temperature of the gas mixture and the flow time, to 9 to 32. This enables to obtain a carbon film which selectively separates alcohols having 2 or less carbon atoms from a liquid mixture of the alcohols having 2 or less carbon atoms and organic compounds having 5 to 9 carbon atoms.

12 Claims, 6 Drawing Sheets

FOREIGN PATENT DOCUMENTS

| | | |
|---|---|---|
| JP | 02-074615 A1 | 3/1990 |
| JP | 10-180046 A1 | 7/1998 |
| JP | 10-180057 A1 | 7/1998 |
| JP | 2000-157843 A1 | 6/2000 |
| JP | 2000-237562 A1 | 9/2000 |
| JP | 2001-232156 A1 | 8/2001 |
| JP | 2006-212480 A1 | 8/2006 |
| JP | 2007-255226 A1 | 10/2007 |
| JP | 2008-106623 A1 | 5/2008 |
| JP | 2008-536043 A1 | 9/2008 |
| WO | 2006/055540 A1 | 5/2006 |
| WO | 2006/108076 A2 | 10/2006 |

OTHER PUBLICATIONS

Shigeharu Morooka et al., "*Microporous Carbon Membranes*," Membrane Science and Technology, 2000, pp. 323-334.

Hidetoshi Kita et al., "*NaY Zeolite Membrane for the Pervaporation Separation of Methanol-Methyl tert-butyl Ether Mixtures*," Chem. Commun. 1997, pp. 45-46.

M.E. van Leeuwen, "*Derivation of Stockmayer Potential Parameters for Polar Fluids*," Fluid Phase Equilibria, vol. 99, 1994, pp. 1-18.

Rosemarie Szostak, "*Handbook of Molecular Sieves*," 1992, 584 pages.

Hans H. Funke et al., "*Separations of Cyclic, Branched, and Linear Hydrocarbon Mixtures through Silicalite Membranes*," Ind. Eng. Chem. Res., vol. 36, 1997, pp. 137-143.

Proceedings of the Society of Chemical Engineers, Japan, 2003, vol. 2003f, p. 546 (with partial English translation).

Shuuzou Ooe, "*Properties Estimation Methods*," Membrane Science and Technology, 6, 2000, pp. 323-334 (with English translation of inventors' derived knowledge taken from Formula (5.68) and (4.13)).

\* cited by examiner

METHOD FOR PRODUCING CARBON FILM, CARBON FILM AND SEPARATOR

TECHNICAL FIELD

The present invention relates to a method for producing a carbon membrane for separating a liquid mixture, a carbon membrane produced by the method, and a separator for a liquid mixture.

BACKGROUND ART

Membrane separation techniques are used in a food and medical field and a water treatment field. In recent years, as represented by application of a membrane separation technique in ethanol production using biomass, i.e., a membrane separation technique of water and ethanol, change of composition of a mixture has been conducted by separating a specific component from a mixture.

Regarding a separation operation of a liquid mixture using a membrane separation technique, in recent years, application to non-aqueous fields, for example, a petroleum refinery process and a petrochemical industry field has been studied (e.g., Patent Documents 1 to 3). For example, Patent Document 2 discloses a separation membrane used for changing a composition of a liquid mixture containing a paraffin-based hydrocarbon liquid and an olefin-based hydrocarbon liquid by a separation operation. Regarding membrane separation techniques, besides such separation of a liquid mixture containing hydrocarbon-based liquids, there has recently been disclosed a trial of application to separation of a liquid mixture containing a hydrocarbon-based liquid and an alcohol liquid for improvement in start-up performance, highly efficient combustion, and cleaning of an internal combustion engine in the fuel field (e.g., Patent Documents 4 to 6).

Patent Document 5 discloses a fuel supplier using a separation membrane using a membrane of an inorganic metal oxide and/or a membrane of a polymer compound to separate a mixed fuel obtained by adding an ethanol fuel to a hydrocarbon-based fuel into a hydrocarbon rich fuel and an ethanol rich fuel. Non-patent Document 1 has a statement that, in a production process of methyl tert-butyl ether (MTBE) or ethyl tert-butyl ether (ETBE) as an octane booster of gasoline, separation of methanol from MTBE or ethanol from ETBE as azeotropic mixtures by a separation membrane is studied.

As a separation membrane for a liquid mixture in a non-aqueous field as described above, a polymer membrane, a zeolite membrane, a carbon membrane, and the like are described. However, the polymer membrane and the zeolite membrane have a defect of low corrosion resistance against an organic solvent or an acid/alkali aqueous solution to deteriorate the performance upon use for a long period.

A carbon membrane is expected to application to separation of a liquid mixture in a non-aqueous field by utilizing the characteristics of a carbon membrane having excellent thermal resistance, acid resistance, and organic solvent resistance (Non-patent Document 2). However, the carbon membrane has a problem of low permeability with high separability or low performance with high permeability. Thinning of the membrane is mentioned as a method for improving the permeability. In this case, there is a problem of deterioration in separability because a defect is easily caused.

There is known a method in which, after a thermosetting resin is formed, it is carbonized and/or activated at 600 to 1100° C. in weak oxidizing atmosphere as a method for enhancing the permeation separability of the carbon membrane for the liquid mixture (Patent Document 7).

As a method for improving permeability of a carbon membrane other than Patent Document 7, there is known a treatment in which a carbon membrane is heated in the presence of oxidizing gas (heating oxidation treatment). For example, in Non-patent Document 3 (FIG. 3), permeability of carbon dioxide and nitrogen improved about 13 times and 40 times, respectively, though separability of carbon dioxide and nitrogen (ratio of permeation rate of carbon dioxide and nitrogen) of the membrane fell from about 30 to 10.

PRIOR ART DOCUMENT

Patent Document

Patent Document 1: JP-A-10-180046
Patent Document 2: JP-A-10-180057
Patent Document 3: JP-A-2000-157843
Patent Document 4: JP-A-2008-106623
Patent Document 5: JP-A-2007-255226
Patent Document 6: JP-A-2008-536043
Patent Document 7: JP-A-2000-237562

Non-Patent Document

Non-patent Document 1: Journal of Membrane Science, 241, 2004, 1-21
Non-patent Document 2: Proceedings of the Society of Chemical Engineers, Japan, Vol. 2003f (2003) P. 546
Non-patent Document 3: Membrane Science and Technology, 6, 2000, 323-334

However, the carbon membrane of Patent Document 7 has low permeability of a liquid mixture and is not satisfactory for practical use. In addition, regarding the carbon material of Non-patent Document 3, improvement in permeability of not a liquid mixture but gas has been confirmed.

The present invention aims to provide a method for producing a carbon membrane having separability similar to that of a conventional membrane and improved permeability, a carbon membrane, and a separator for a liquid mixture.

SUMMARY OF THE INVENTION

The present inventors found out that the aforementioned problems could be solved by treating a carbon membrane by a gas mixture containing oxidizing gas. That is, according to the present invention, there are provided the following method for producing a carbon membrane, carbon membrane produced by the method, and separator.

[1] A method for producing a carbon membrane, the method comprising thermally decomposing a carbon-containing layer as a precursor in an oxygen inert atmosphere to obtain a carbon membrane and then subjecting the carbon membrane to a heating oxidation treatment while sending a gas mixture containing oxidizing gas thereinto to obtain the carbon membrane which selectively separates alcohols having 2 or less carbon atoms from a liquid mixture of the alcohols having 2 or less carbon atoms and organic compounds having 6 to 9 carbon atoms.

[2] The method for producing a carbon membrane according to [1], wherein the carbon membrane is subjected to the heating oxidation treatment while sending the gas mixture so that (temperature ° C.)$^2$×hour (h)/10000, which shows a relation between temperature of the gas mixture and time for sending the gas mixture is within the range from 9 to 32.

[3] The method for producing a carbon membrane according to [1] or [2], wherein the carbon membrane is subjected to the heating oxidation treatment while sending the gas mixture so that the ratio of a flow rate of the gas mixture to an area of the carbon membrane is 0.5 cm/min. or more.

[4] The method for producing a carbon membrane according to any one of [1] to [3], wherein the oxidizing gas is oxygen.

[5] The method for producing a carbon membrane according to any one of [1] to [4], wherein the carbon-containing layer as a precursor is a resin layer.

[6] The method for producing a carbon membrane according to any one of [5], wherein the resin forming the resin layer is at least one kind selected from the group consisting of polyimide based resins and phenol based resins.

[7] The method for producing a carbon membrane according to any one of [1] to [6], wherein the carbon-containing layer is formed on a porous ceramic substrate.

[8] The method for producing a carbon membrane according to [7], wherein the carbon membrane is formed after thermal decomposition of the carbon-containing layer in the oxygen inert atmosphere and before the heating oxidation treatment so that carbon membrane has at least a composite layer formed in the porous ceramic substrate and that the mass of the surface carbon membrane layer/(mass of the surface carbon layer+mass of the composite layer) is 0.5 or less in a relation between the composite layer and the surface carbon membrane layer of the carbon membrane formed and exposed on a surface of the porous ceramic substrate.

[9] The method for manufacturing a carbon membrane according to [8], wherein the carbon membrane is formed so that the carbon membrane has only a composite layer without having the surface carbon membrane layer after thermal decomposition of the carbon-containing layer in the oxygen inert atmosphere and before the heating oxidation treatment.

[10] A carbon membrane produced by a method for producing a carbon membrane according to any one of [1] to [9].

[11] The carbon membrane according to [10], wherein the carbon membrane is formed on a porous ceramic substrate and has a composite layer formed in the porous ceramic substrate, and the mass of the surface carbon membrane layer/ (mass of the surface carbon layer+mass of the composite layer) is 0.5 or less in the relation between the composite layer and the surface carbon membrane layer of the carbon membrane formed and exposed on a surface of the porous ceramic substrate.

[12] The carbon membrane according to [10] or [11], wherein the carbon membrane is formed on the porous ceramic substrate and has only a composite layer formed in the porous ceramic substrate without being exposed on the surface of the porous ceramic substrate.

[13] A separator for the liquid mixture using a carbon membrane according to any one of [10] to [12].

According to a production method of the present invention, there can be produced a carbon membrane having high separability in separation of a liquid mixture and improved permeability.

MODE FOR CARRYING OUT THE INVENTION

Hereinbelow, an embodiment of the present invention will be described with referring to drawings. The present invention is not limited to the following embodiment, and changes, modifications, and improvements may be obtained as long as they do not deviate from the scope of the invention.

A method for producing a carbon membrane of the present invention is a method of obtaining a carbon membrane by thermal decomposition of a carbon-containing layer as a precursor in an oxygen inert atmosphere and thermally oxidizing the carbon membrane while sending a gas mixture containing oxidizing gas. This enables to obtain a carbon membrane which selectively separates alcohols having 2 or less carbon atoms from a mixture (hereinbelow, sometimes referred to as a liquid mixture) of the alcohols having 2 or less carbon atoms and organic compounds having 6 to 9 carbon atoms. It is preferable to send the gas mixture so that (temperature ° C.)$^2$×time (h)/10000, which shows a relation between temperature of the gas mixture and time for sending the gas mixture, is within the range from 9 to 32. Further, it is preferable that the gas mixture is sent so that the ratio of a flow rate of the gas mixture to an area of the carbon membrane is 0.5 cm/min. or more. The oxidizing gas is preferably oxygen. The carbon-containing layer as a precursor is preferably a resin layer. In addition, the resin forming the resin layer is preferably at least one kind selected from the group consisting of polyimide based resins and phenol based resins. Further, it is preferable that the carbon-containing layer is formed on a porous ceramic substrate.

A carbon membrane of the present invention is a carbon membrane obtained by the aforementioned production method and capable of being used for separation of a liquid mixture. In addition, a separator of a liquid mixture of the present invention is a separator using the carbon membrane as the separation membrane.

In the first place, a carbon membrane of the present invention will be described more specifically. A carbon membrane of the present invention is substantially made of carbon and selectively separates alcohols having 2 or less carbon atoms from a liquid mixture of the alcohols having 2 or less carbon atoms and organic compounds having 6 to 9 carbon atoms. More specifically, it is a porous carbon membrane substantially made of carbon and disposed on a surface of a porous substrate. In the present specification, "is substantially made of carbon" means that carbon is contained at 50% or more as a mass proportion.

Figure 1:
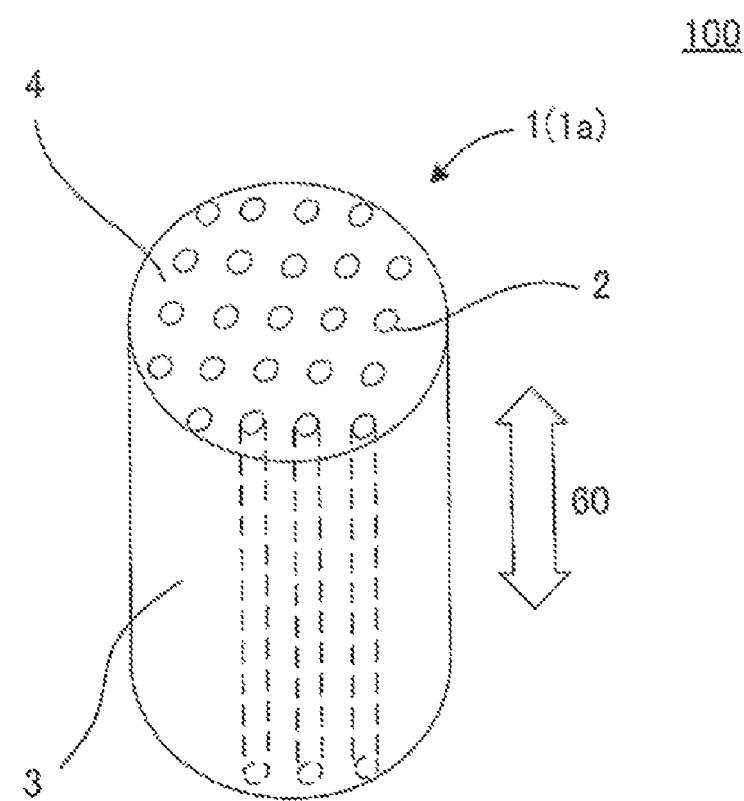
FIG. 1 is a view showing an embodiment of a separation membrane-provided body where a carbon membrane of the present invention is disposed.

FIG. 1 shows an embodiment of a separation membrane-provided body 100 where a carbon membrane 11 of the present invention is disposed. The carbon membrane 11 is formed on the porous substrate 1 (see FIG. 3), functions as a separation membrane, used in a state of a separation membrane-provided body 100 where the separation membrane (carbon membrane 11) and porous substrate 1 supporting the membrane are unitarily joined. The carbon membrane 11 is formed on the inner wall faces 5 of the through-holes 2 formed along the longitudinal direction 60 of the porous substrate 1 of the monolith shape, and seal portions 12 are disposed on both the end faces 4, 4. The seal portions 12 are disposed on the entire end faces 4, 4 of the porous substrate 1 (monolith-shaped substrate 1a) lest the through-holes 2 should be covered.

The separation membrane-provided body 100 separates a liquid mixture by sending the liquid mixture into the through-holes 2 from the open portion 51 of each of the through-holes 2 of the monolith-shaped substrate 1a, passing part of the liquid mixture (passing fluid) through the carbon membrane 11 disposed on the inner wall faces 5 of the through-holes 2 to flow into the inside of the monolith-shaped substrate 1a, and discharging the liquid mixture outside from the side face 3 of the monolith-shaped substrate 1a. The seal portions 12 inhibit the liquid mixture entering the inside of the monolith-shaped substrate from the end face 4 of the monolith-shaped substrate 1a from being mixed with the passing fluid having passed through the carbon membrane 11 and discharged from the side face 3.

In the separation membrane-provided body 100 of the present embodiment, there is no limitation on the material for the porous substrate 1 as long as it has sufficient strength, permeability, corrosion resistance, and the like, and metals or ceramics may be used. It is preferable to use a porous substrate made of ceramics. For the ceramics particles, alumina, silica, cordierite, zirconia, mullite, or the like, is preferable. The average pore size of the porous substrate is preferably 0.01 to 10 more preferably 0.05 to 5 µm. In addition, the porosity is preferably 20 to 80%, more preferably 30 to 70%.

There is no particular limitation on the shape of the porous substrate 1, and the shape can be determined according to the purpose from a disc shape, a polygonal plate shape, a cylindrical shape such as a circular cylindrical shape or a prismatic cylindrical shape, a columnar shape such as a circular columnar shape or a prismatic columnar shape, and the like. In addition, the size of the porous substrate 1 is not particularly limited and can be determined according to the purpose in the range where necessary strength as a support can be satisfied and where permeability of the fluid to be separated is not impaired. Since the ratio of the membrane area to the capacity is large, particularly a monolith shape as shown in FIG. 1 is desirable. The "monolith-shaped substrate" means a lotus root-shaped or honeycomb-shaped substrate where a plurality of through-holes are formed in the longitudinal direction 60.

There is no particular limitation on the shape of a carbon membrane 11 of the present invention. The shape may be, for example, a stick-like shape, a pellet-like shape, a flat plate-like shape, a tube-like shape, a monolith shape, a honeycomb shape, or the like with the aforementioned porous substrate 1 as a support. Since the ratio of the membrane area to the capacity of the substrate can be made large, it is particularly preferable that the membrane is formed on the inner wall faces 5 of the through-holes 2 of the monolith-shaped substrate shown in FIG. 1.

The carbon membrane 11 can be obtained by thermally decomposing a carbon-containing layer as a precursor in an oxygen inert atmosphere for carbonization and further thermally oxidizing it. The carbon-containing layer is preferably a resin layer. Though there is no particular limitation on the precursor for obtaining a carbon membrane by thermal decomposition as long as it contains carbon, it is preferably formed of polyimide-based resin, phenol-based resin, or the like. In addition, the thermal decomposition is performed at preferably 400 to 1000° C., more preferably 450 to 900° C. The oxygen inert atmosphere means an atmosphere where the precursor for the carbon membrane is not oxidized even by heating in the aforementioned temperature range. Specifically, it is an atmosphere of inert gas such as nitrogen or argon or a vacuum atmosphere. The heating oxidization treatment after carbonization is performed in gas containing at least oxide gas. The oxide gas is oxygen, water vapor, carbon dioxide, or a gas mixture of the aforementioned gas and gas inert against carbon, such as nitrogen, argon, and helium.

The membrane thickness of the carbon membrane 11 is preferably 0.01 to 10 µm, more preferably 0.05 to 5 µm. When it is smaller than 0.01 µm, a defect may be caused in the membrane. When it is larger than 10 µm, a permeation flux upon separation may decrease. The average pore size of the carbon membrane 11 is preferably 0.2 to 100 nm, more preferably 0.2 to 10 nm. The average pore size can be measured by a gas adsorption method.

Figure 4:
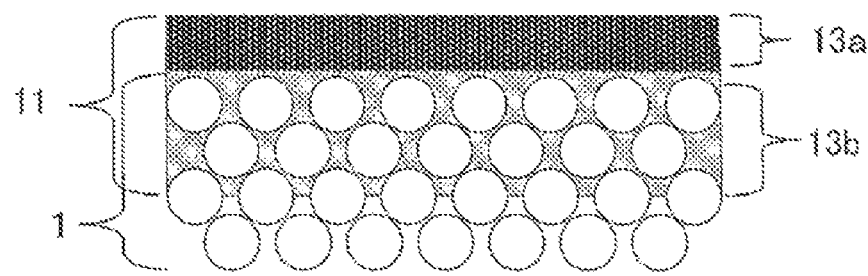
FIG. 4 is a cross-sectional schematic view of the vicinity of the boundary face between the porous substrate and the carbon membrane.

The carbon membrane 11 is formed on the porous ceramic substrate as shown in FIG. 4, and it is preferable that the carbon membrane 11 has at least a composite layer 13b formed in the porous ceramic substrate. Further, the mass of the surface carbon membrane layer/(mass of the surface carbon layer+mass of the composite layer) is preferably 0.5 or less in a relation between the composite layer 13b and the surface carbon membrane layer 13a of the carbon membrane 11 formed and exposed on a surface of the porous ceramic substrate. It is more preferably 0.2 or less, and the carbon membrane 11 is preferably formed to have only the composite layer 13b without having the surface carbon membrane layer 13a.

The seal portion 12 (see FIG. 3) may be a glass seal or a metal seal. Of these, a glass seal is preferable because it is excellently easy to match the thermal expansion coefficient with that of the porous substrate. Though there is no particular limitation on the properties of the glass used for the glass seal, it is preferable to have a thermal expansion coefficient close to that of the porous substrate. In addition, nonlead glass not containing lead or the like is preferable as the glass used for the glass seal.

Next, description will be made regarding a production method of a carbon membrane 11 of the present invention. A porous substrate 1 to serve as a substrate for forming the carbon membrane 11 thereon is produced by, for example, extrusion and firing in a method for producing a conventional porous monolith-shaped substrate 1a.

Figure 2:
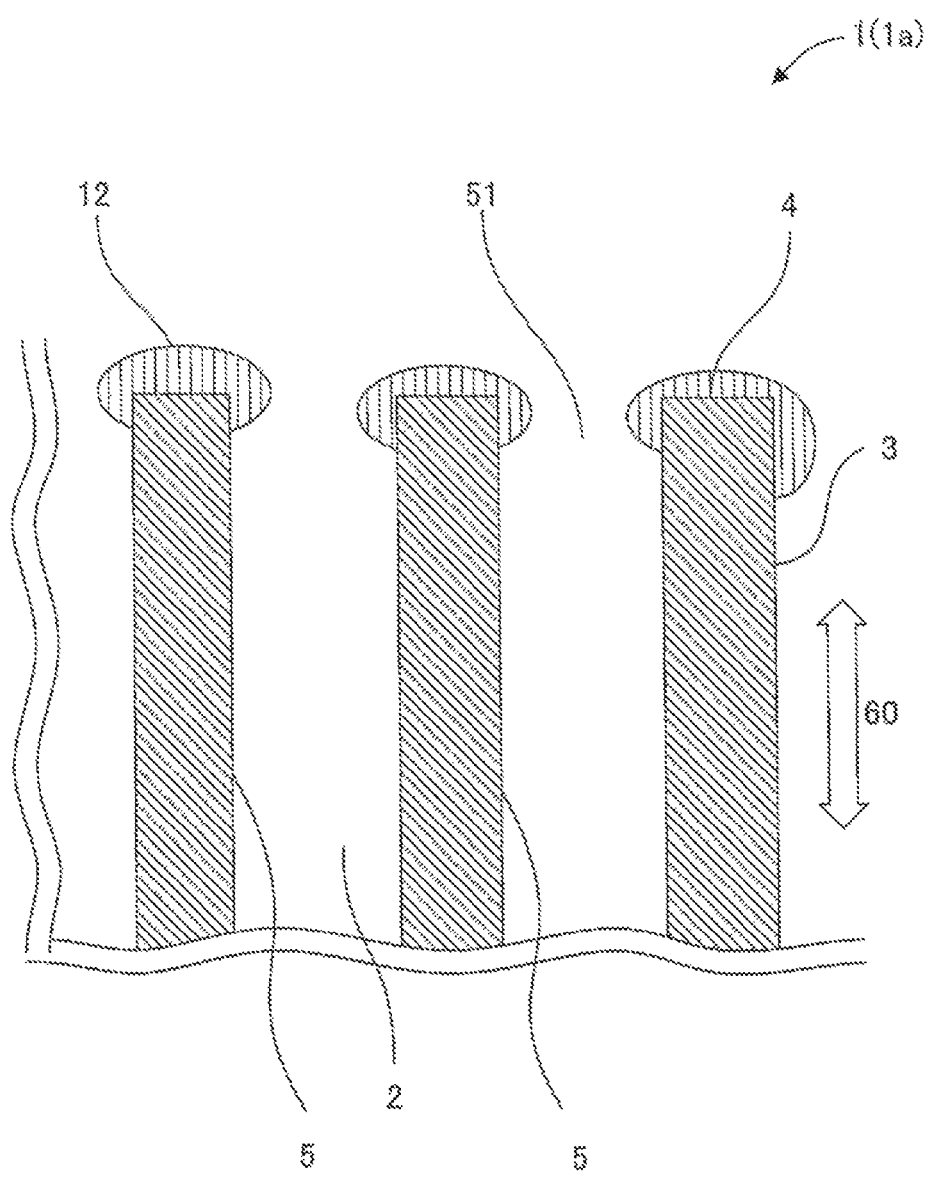
FIG. 2 is a cross-sectional view of an end face and the vicinity of the outer peripheral face of a porous substrate before a carbon membrane is disposed.

Next, a glass paste is applied on both the end face of the porous substrate and heated at predetermined temperature to form seal portion 12 as shown in FIG. 2. In the first place, a glass paste is applied on a surface of the porous substrate 1. There is no particular limitation on the portion where the glass paste is applied, and it is preferable to apply the glass paste on a portion where gas, liquid, micro particles, and the like are inhibited from traveling from inside the porous substrate 1 to the outside or from the outside to the inside of the porous substrate 1 on the surface of the porous substrate 1. In the present embodiment, the glass paste is applied on both the end faces 4, 4 of the porous substrate 1 (monolith-shaped substrate 1a).

Nonlead glass not containing lead is preferable as the glass material applied on the surface of the porous substrate 1 as the glass paste. The softening point of the glass material is preferably 600 to 1000° C., more preferably 700 to 1000° C. When it is lower than 600° C., glass may melt upon heating in the step of forming the carbon membrane 11. When it is higher than 1000° C., the sintering of the particles constituting the porous substrate 1 may proceed more than necessary. The glass paste can be produced by dispersing powdershaped glass in a solvent such as water. In addition, it may be produced by adding polymer or the like to the solvent such as water.

Next, there is performed a membrane-forming step where a membrane made from a precursor solution for a carbon membrane 11 is formed on a porous substrate 1. In a membrane-forming step, there is no particular limitation on the method for passing the precursor solution through the through-holes 2 of the monolith-shaped substrate 1a. However, a dip forming method is suitable.

As the precursor solution used for forming a membrane in a membrane-forming step of an embodiment of the present invention to obtain a carbon membrane, it is preferable to use a polyimide solution and/or a phenol solution. The polyimide solution and/or the phenol solution are/is obtained by dissolving a polyimide resin and/or a phenol resin in an appropriate organic solvent such as N-methyl-2-pyrrolidone (NMP). Though there is no particular limitation on the concentration of polyimide and/or phenol in the polyimide solution and/or the phenol solution, it is preferably 1 to 15 mass % from the viewpoint of imparting a viscosity for easy formation to the solution. Incidentally, by controlling the membrane-forming conditions such as temperature of the precursor solution, the ratio of the surface carbon membrane layer 13a and the composite layer 13b of the carbon membrane 11 can be controlled (see FIG. 4).

Next, a drying step for drying the membrane (carbon-containing layer) of the precursor solution is performed. In the drying step, for example, circulation drying of the membrane of a precursor solution is performed by passing hot air from the open portion 51 of one end face 4 toward the open portion 51 of the other end face 4.

Figure 3:
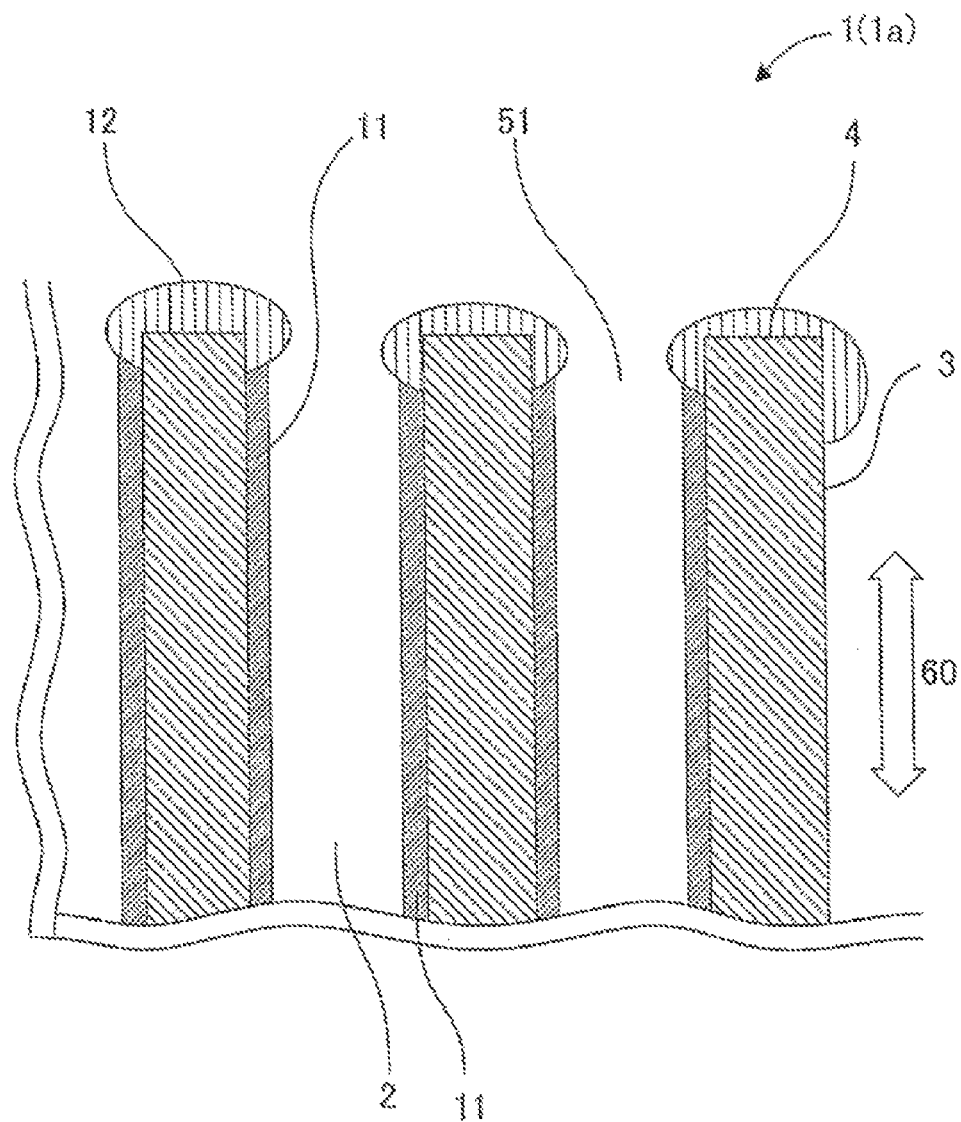
FIG. 3 is a cross-sectional view of an end face and the vicinity of the outer peripheral face of a porous substrate having a carbon membrane disposed thereon.

After the drying step, polyimide membrane and/or a phenol membrane is subjected to a heating treatment step (carbonization) in an inert atmosphere such as a vacuum or nitrogen atmosphere or an argon atmosphere. By the carbonization by thermal decomposition in a temperature range from about 400 to 1000° C., a carbon membrane 11 as shown in FIG. 3 is obtained. That is, the carbon membrane 11 can be obtained by carbonizing by thermally decomposing the carbon-containing layer (resin layer) as a precursor in an oxygen inert atmosphere. Generally, when carbonization is performed at temperature of below 400° C., the polyimide membrane and/or the phenol membrane are/is not carbonized sufficiently to decrease selectivity and permeation rate as a separation membrane. On the other hand, when carbonization is performed at temperature of above 1000° C., the pore diameter shrinks to decrease the permeation rate. Incidentally, the oxygen inert atmosphere means an atmosphere where the precursor for the carbon membrane is not oxidized even by heating in the aforementioned temperature range. Specifically, it is an atmosphere of inert gas such as nitrogen or argon or a vacuum atmosphere.

As shown in FIG. 4, it is preferable that the carbon membrane 11 is formed after thermal decomposition of the carbon membrane in the oxygen inert atmosphere and before the heating oxidation treatment so that carbon membrane 11 has at least a composite layer 13b formed in the porous ceramic substrate and that the mass of the surface carbon membrane layer/(mass of the surface carbon layer+mass of composite layer) is 0.5 or less in a relation between the composite layer 13b and the surface carbon membrane layer 13a of the carbon membrane formed and exposed on a surface of the porous ceramic substrate. The proportion is more preferably 0.2 or less, and it is more preferable to form the carbon membrane 11 so that the carbon membrane 11 has only the composite layer 13b without having the surface carbon membrane layer 13a. Thus, by forming the carbon membrane 11 and subjecting the membrane 11 to the heating oxidation treatment by a gas mixture containing oxidizing gas, the separability of the carbon membrane 11 can be improved. Though the reason is unknown, it is guessed as follows. Upon the heating oxidation treatment by a gas mixture containing oxidizing gas, decomposition or thermal expansion due to the reaction of the carbon membrane 11 with the oxidizing gas causes the change in volume, and a crack is easily caused as a defect. However, in the case that the mass of the surface carbon membrane layer is in the aforementioned proportion, since the entire carbon membrane is restrained moderately by the composite layer 13b of the substrate and the carbon membrane 11, the crack generation is suppressed. Therefore, the smaller the surface carbon membrane layer 13a is, the higher the separability after the heating oxidation treatment becomes. Incidentally, the ratio of the surface carbon membrane layer 13a to the composite layer 13b can be controlled by the membrane-forming conditions such as a concentration of the precursor solution.

Figure 5:
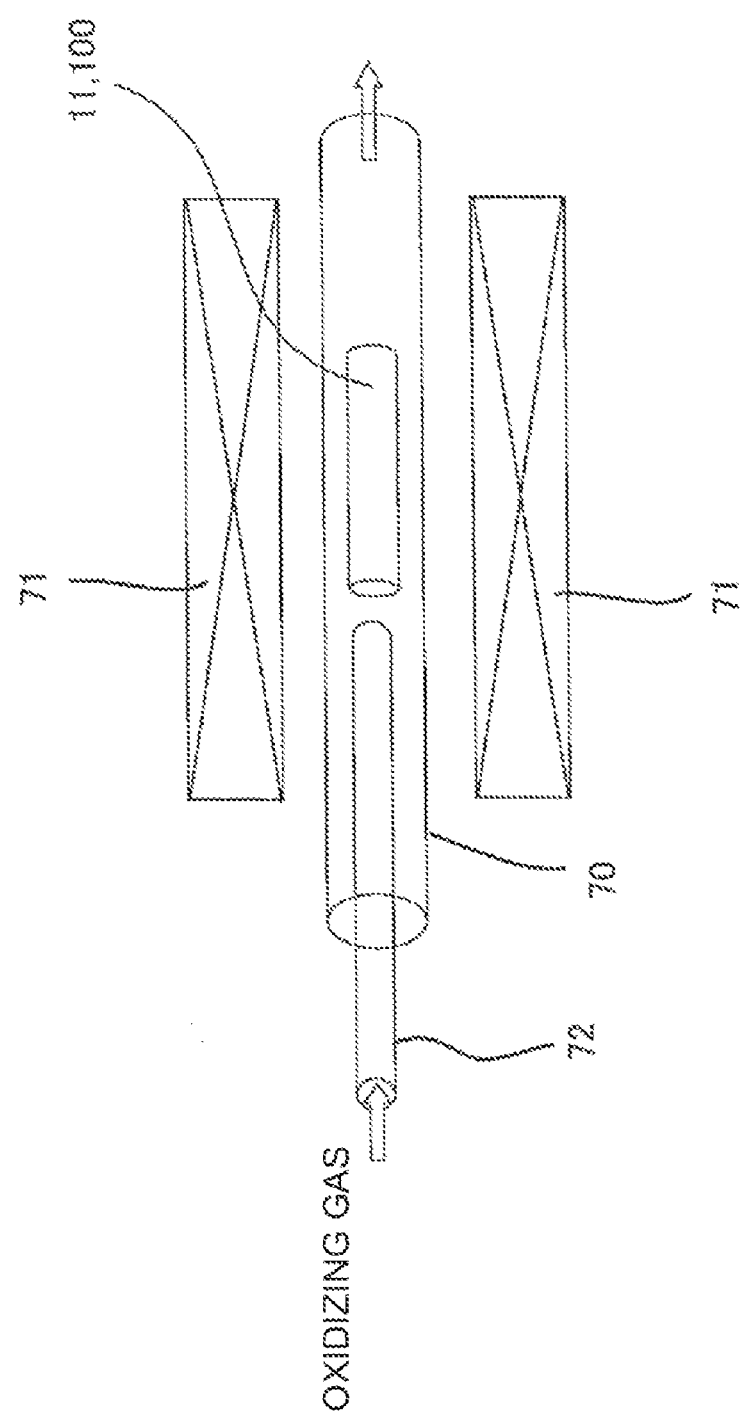
FIG. 5 is a schematic view showing an apparatus used for a thermal oxidization treatment.

Next, the carbon membrane 11 obtained by subjecting a carbon-containing layer to thermal decomposition for carbonization is subjected to the heating oxidation treatment. The heating oxidation treatment means a heating treatment in gas containing at least oxidizing gas. Specifically, the carbon membrane 11 is maintained in the heating furnace where a mixed gas containing oxidizing gas is sent as an example. The heating oxidation treatment is performed by the use of a heating furnace into which a gas mixture containing oxidizing gas can flow and in which the inside atmosphere can be made only the gas mixture. The carbon membrane 11 is disposed in such a manner that the surface of the membrane is parallel to the flow direction of the gas mixture. However, when the separation membrane-provided body 100 has a monolith shape, gas cannot reach the membrane surface inside the monolith (separation membrane-provided body 100) simply by maintaining the membrane in the heating furnace. Therefore, it is necessary to sufficiently supply the oxidizing gas on the membrane surface inside the monolith. For example, as shown in FIG. 5, a separation membrane-provided body 100 having a carbon membrane 11 formed thereon is put in a hollow body (e.g., ceramic tube 70) in order to inhibit the gas mixture from diffusing, and they are put in a heating furnace 71. Then, the heating oxidation treatment may be performed with introducing the gas mixture into the vicinity of the separation membrane-provided body 100 by a SUS tube 72, which is a gas introduction tube. By reducing the gap between the ceramic tube 70 and the monolith (separation membrane-provided body 100) on a face perpendicular to the gas mixture flow direction, the oxidizing gas can be supplied sufficiently to the surface of the carbon membrane 11 inside the monolith.

As the oxidizing gas, there can be used water vapor, carbon dioxide, or a gas mixture of such gas and gas inert against carbon, such as nitrogen, argon, and helium. However, since these cases need high temperature in order to obtain an affect in comparison with the case of using oxygen, gas containing oxygen is more preferable as the oxidizing gas.

The supply flow rate of the gas mixture containing oxidizing gas is balanced with the area of the carbon membrane subjected to the heating oxidation treatment. The ratio (R) of the supply flow rate of the gas mixture to the area of the membrane subjected to the heating oxidation treatment is preferably 0.5 cm/min. or more, more preferably 1.4 cm/min. or more. Though there is no particular limitation on the upper limit of R, about 1.4 cm/min. is sufficient from the economical viewpoint because the effect is not changed even by excess supply of the oxidizing gas.

The temperature of the heating oxidation treatment is preferably 250 to 450° C., more preferably 300 to 400° C. The effect of the heating oxidation treatment cannot be obtained at below 250° C., and the carbon membrane disappears by the oxidizing gas at above 450° C., and thereby sufficient separation performance cannot be obtained. When the heating oxidation treatment time is too short, there is no effect. When the heating oxidation treatment time is too long, the carbon membrane disappears. However, the appropriate time depends on the treatment temperature. The heating oxidation time and temperature are preferably set so that A shown in the following formula is within the range from 9 to 32.

$$A = (\text{temperature}[° C.])^2 \times (\text{time}[h])/10000$$

The mass of the surface carbon membrane layer/the mass of the entire carbon membrane of the carbon membrane 11 after the heating oxidation treatment is not changed from that before the heating oxidation treatment. That is, after the heating oxidation treatment, the mass of the surface carbon membrane layer/(mass of the surface carbon layer+mass of the composite layer) is preferably 0.5 or less, more preferably 0.2 or less.

The composition of the liquid mixture can be changed by the use of a carbon membrane 11 of the present invention produced by performing the aforementioned heating oxidation treatment. Specifically, the liquid mixture of alcohols having 2 or less carbon atoms and organic compounds having 6 to 9 carbon atoms is bought into contact with a face on one side of the carbon membrane (supply side face), and the alcohol having 2 or less carbon atoms is preferentially permeated (discharged), and thereby the composition of the liquid mixture can be changed. Incidentally, the liquid mixture may be heated to be supplied as vapor. The alcohol having 2 or less carbon atoms means methanol and ethanol. In addition, an organic compound having 6 to 9 carbon atoms means ether, carboxylic acid, ester, alcohol, chain hydrocarbon, and cyclic hydrocarbon having 6 to 9 carbon atoms. As an example, ethanol can preferentially be permeated out of a liquid mixture of ethanol and gasoline.

It is known that separation by a membrane is based on the sieving (molecular sieve effect) by pores of the membrane the difference in affinity (adsorption effect) between the membrane and molecules. Therefore, in membrane separation, the size of the pores exhibiting the separation is different depending on the combination with a target for separation even if the material of the membrane is the same. According to a heating oxidation treatment described in the present application, since the pores can have the maximum size in the range where the separability of alcohol is not impaired to a large extent in separation of alcohol from a liquid mixture, a carbon membrane having high permeation separability can be obtained.

As a method for enhancing the permeation separability of a carbon membrane for a liquid mixture besides a method where a carbon membrane is subjected to a heating oxidation treatment described in the present application, there is known a method where, after a thermosetting resin (carbon-containing layer) as a precursor is formed, it is carbonized and/or activated in a temperature range of 600 to 1000° C. in a weak oxidizing atmosphere (Patent Document 7). In the Patent Document 7, carbon dioxide and water vapor are described as weak oxidizing atmosphere. However, it is possible to obtain a similar effect by a gas mixture of a minute amount of oxygen and inert gas such as nitrogen or argon. However, the method where a carbon-containing layer is carbonized by a gas mixture containing a minute amount of oxygen has a problem of unstable permeation separability of the membrane when a carbon membrane having a practical size is produced by a large furnace. It is presumed that the reason is because, though it is necessary to maintain very low concentration of several hundred ppm or less since oxygen has very high activity against a carbon-containing layer, it is difficult to maintain the oxygen in the furnace uniformly at such very low concentration. Therefore, as a method for enhancing the separability of a carbon membrane for a liquid mixture, a method where a carbon membrane obtained by subjecting a carbon-containing layer as a precursor described in the present application in an oxygen inert atmosphere is subjected to a heating treatment with sending a gas mixture containing oxidizing gas is considered to be excellent practically.

The method for changing the composition of the liquid mixture of the present invention is a method where the composition of the liquid mixture is changed by the use of the aforementioned carbon membrane 11. The method may be a method where gas is permeated by supplying a liquid mixture as liquid (pervaporation method) or a method where the entire liquid is once vaporized by heating to allow the gas to permeate (vapor permeation). Alternatively, the liquid may be heated until a part of the liquid is vaporized to allow the gas to be permeated.

Figure 6:
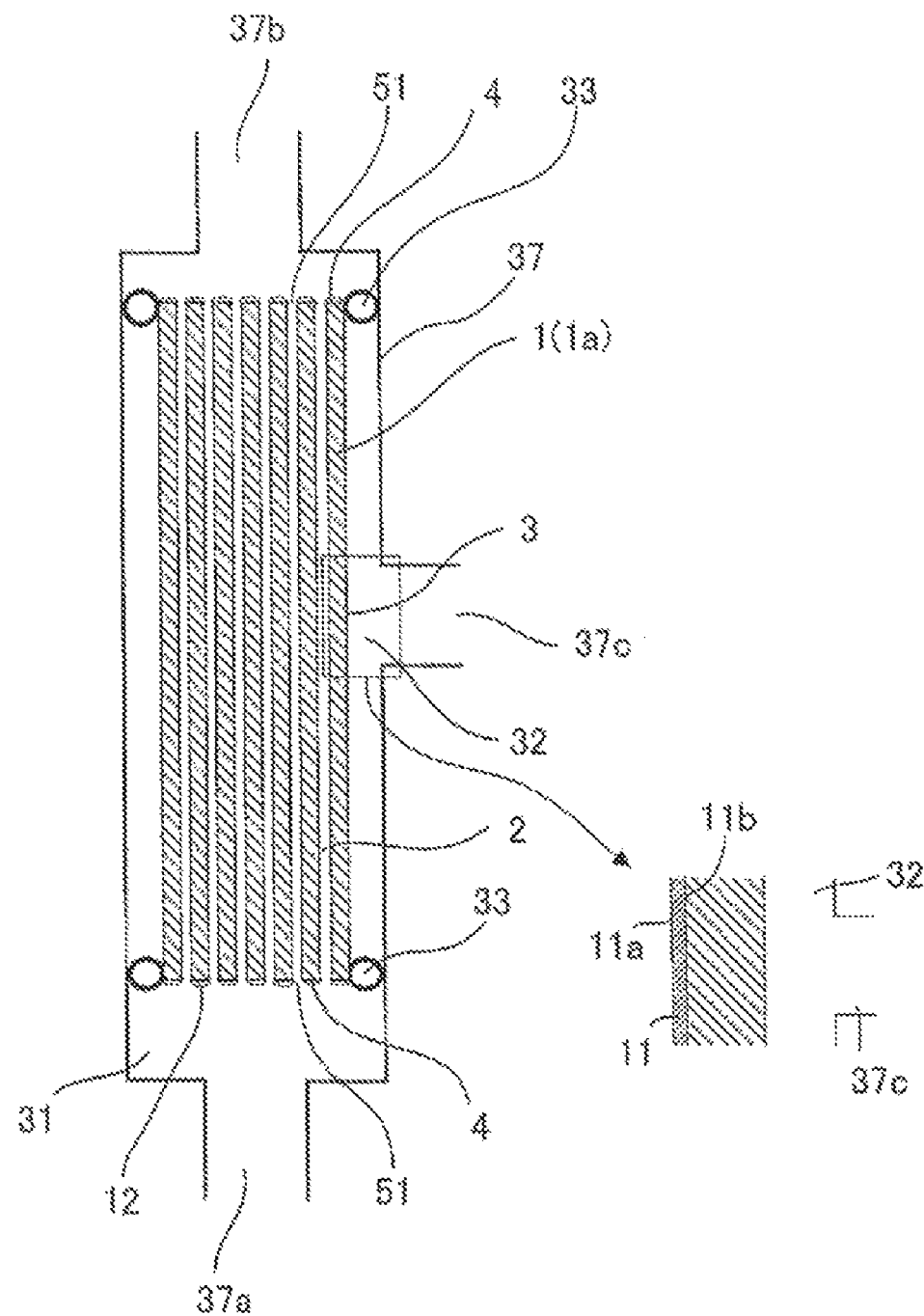
FIG. 6 is a cross-sectional view showing a SUS module provided with a porous substrate having a carbon membrane of the present invention disposed thereon.
Figure 7:
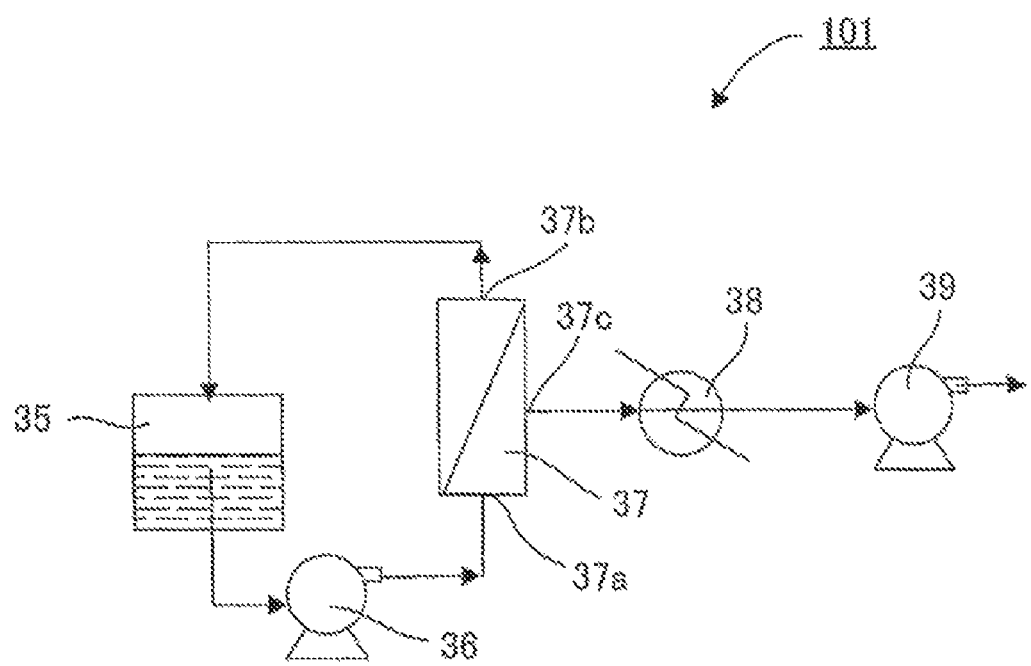
FIG. 7 is a schematic view showing an embodiment of a separator.

In addition, the separator of the liquid mixture of the present invention is a separator of a liquid mixture using the aforementioned carbon membrane. Specifically, it is a separator 101 as shown in FIG. 6 and FIG. 7. That is, a separator 101 of the present invention comprises a separation portion for separating a raw material side space from a permeation side space, a supply portion for supplying a liquid mixture to the raw material side space, and a permeation collection portion for collecting permeated liquid and/or permeated gas which have/has permeated through the carbon membrane from the permeation side space. The separation portion is provided with the aforementioned carbon membrane 11 and constituted of a SUS module 37 having a porous substrate 1 supporting the carbon membrane 11. In addition, a supply portion is constituted of a raw material tank 35 and a circulation pump 36, and the permeation collection portion is constituted of a cooling trap 38 as a cooler and a vacuum pump 39.

The raw material tank 35 heats and maintains a liquid mixture (raw material) containing an alcohol and an organic compound contained in the tank at predetermined temperature (e.g., 50° C.).

On the SUS module 37, a supply liquid introduction port 37a and a supply liquid discharge port 37b are formed so as to communicate with the raw material side space 31, and the permeated vapor collection port 37c for discharging the permeated vapor outside is formed in the permeation side space 32. The liquid mixture of the raw material tank 35 is constituted to be supplied to the raw material side space 31 of the SUS module 37 by the circulation pump 36.

The SUS module 37 shown in FIG. 6 is constituted so that the monolith-shaped substrate 1a where a carbon membrane is formed can be disposed at a predetermined position of the outer peripheral portion of both the ends by means of an O-ring 33. The SUS module 37 is separated into the raw material side space 31 and the permeation side space 32 by the O-ring 33, the glass seal (sealing portion 12) and the carbon membrane 11.

A cooling trap 38 and a vacuum pump 39 are provided on the permeated vapor collection port 37c side of the SUS module 37, and the permeated vapor discharged from the permeated vapor collection port 37c is collected in the liquid N₂ trap.

By the aforementioned constitution, a raw material is circulated by supplying the raw material to the raw material side space 31 of the SUS module 37 from the supply liquid introduction port 37a by a circulation pump 36, and the raw material discharged from the supply liquid discharge port 37b is returned to the raw material tank 35. The separation method of the liquid mixture of the present invention employs the aforementioned liquid mixture as the raw material. The liquid mixture is used as a supply liquid mixture, and at least a part of the supply liquid mixture is brought into contact with the carbon membrane on the membrane supply side 11a in a state of liquid from the supply liquid introduction port 37a. By reducing the pressure on the support side of the carbon membrane 11 by the vacuum pump 39, the permeated vapor permeating to the membrane permeation side 11b of the carbon membrane 11 and being discharged from the permeation vapor collection port 37c is collected in the liquid N₂ trap. The degree of vacuum of the permeation side space 32 is controlled to predetermined pressure (e.g., about 0.5 Torr) by a pressure controller. This enables to change the composition of the liquid mixture.

EXAMPLE

The present invention will be described in more detail on the basis of Examples. However, the present invention is by no means limited to these Examples.

<Production of Porous Substrate>

There was produced a circular columnar substrate made of porous alumina (monolith-shaped substrate 1a, porous ceramic substrate) having a diameter of 30 mm and a length of 160 mm, and having 55 straight through-holes (through-holes 2) of a diameter of 2.5 mm along the longitudinal direction 60 by extrusion and firing. Further, sealing was performed on both the end portions 4, 4 of the monolith-shaped substrate 1a by melting glass (sealing portion 12) and subjected to the test described below (see FIG. 2).

<Production of Carbon Membrane>

A solution (5 to 15 mass %) obtained by dissolving a commercially available phenol based resin (Bellpearl S899 produced by Air Water, Inc.) in a solvent was dip-coated on the inner faces of the straight through-holes 2 of the monolith-shaped substrate 1a to form a coat layer. A hot air was sent into the straight through-holes 2, and, after the solvent was almost dried, it was dried for one hour at 300° C. in the atmosphere by a drier. The step was repeated 2 to 5 times to form a resin layer (carbon-containing layer) on the inner faces of the straight through-holes 2 of the monolith-shaped substrate 1a. In order to measure the density of the resin layer formed above, vacuuming was performed by a commercially available rotary vacuum pump via the resin layer, it was confirmed that it reached 100 Pa or less. The monolith-shaped substrate 1a having the resin layer formed thereon was subjected to a thermal treatment for one hour (temperature rise rate of 300° C./h) at 550° C. in a nitrogen atmosphere as an oxygen inert atmosphere for thermal decomposition, thereby carbonizing the resin layer to obtain a carbon membrane 11 (separation membrane) formed on the inner faces of the through-holes 2 of a monolith-shaped substrate 1a. The carbon content in the carbon membrane was measured and was 90 mass % or more. The mass of the surface carbon membrane layer/the mass of the entire carbon membrane in the carbon membrane after carbonization (after the thermal decomposition of the carbon-containing layer in the oxygen inert atmosphere and before the heating oxidation treatment) in each Example is shown in Table 1 (mass of entire carbon membrane=mass of surface carbon membrane layer+mass of composite layer).

<Heating Oxidation Treatment of Carbon Membrane>

The carbon membrane obtained by carbonization was subjected to a heating oxidation treatment. As shown in FIG. 5, the heating oxidation treatment was performed by putting the separation membrane-provided body 10 having a carbon membrane 11 formed thereon in a ceramic tube 70 and putting them in a heating furnace 71 with sending a gas mixture containing oxidizing gas into the furnace. The conditions of the heating oxidation treatment are shown in Tables 1 and 2. The mass of the surface carbon membrane layer/the mass of the entire carbon membrane in the carbon membrane after the heating oxidation treatment in each Example is shown in Table 1. In any of the Examples, the mass of the surface carbon membrane layer/the mass of the entire carbon membrane after the heating oxidation treatment was not changed from that before the heating oxidation treatment.

<Performance Evaluation Test of Carbon Membrane, Pervaporation Test>

Pervaporation test was performed by the use of an apparatus (separator 101) shown in FIG. 7 to carry out performance evaluation of the membrane. The liquid mixture (having sufficient volume with respect to the apparatus system), which was a raw material, put in a raw material tank 35 was heated and maintained at predetermined temperature (e.g., 50° C.). The monolith-shaped substrate 1a having the carbon membrane 11 formed thereon was put in a SUS casing via the O-ring 33 on the outer peripheral portion of both the ends to obtain a SUS module 37, which was then disposed at a predetermined position.

The SUS module 37 was separated into a raw material side space 31 and a permeation side space 32 by a glass seal (seal portion 12) and a carbon membrane 11. The raw material was supplied to the raw material side space 31 of the SUS module 37 from the supply liquid introduction port 37a by a supply pump (circulation pump 36), and the raw material discharged from the supply liquid discharge port 37b was returned to the raw material tank 35 for circulation of the raw material. The linear velocity upon circulation was 1.4 m per second. The permeated vapor having permeated through the carbon membrane 11 by reducing the pressure on the support side of the carbon membrane 11 by a vacuum pump 39 and discharged from the permeated vapor collection port 37c was collected in a liquid nitrogen trap (cooling trap 38). The degree of vacuum of the permeation side space 32 was controlled to have predetermined reduced pressure (e.g. about 0.5 Torr) by a pressure controller. On the SUS module 37, a supply liquid introduction port 37a and a supply liquid discharge port 37b were formed so as to communication with the raw material side space 31, and a permeated vapor collection port 37c for discharging the permeated vapor outside was formed in the permeation side space 32.

The performance evaluations (separability, permeation flux) of the carbon membrane 11 were carried out by conducting pervaporation by the apparatus, subjecting the liquefied material of the permeated vapor collected in the liquid nitrogen trap (cooling trap 38) to gas chromatography analysis, and determining quantity of the composition of the permeated vapor. The judgment of the separability was performed depending on whether the mass % of methanol or ethanol of the permeated liquid is higher or lower than mass % of the vapor composition in equilibrium with the supply liquid. That is, if the mass % of methanol or ethanol of the permeated liquid is higher than mass % of methanol or ethanol of a gas-liquid equilibrium vapor of the supply liquid, the membrane is regarded as effective for separation.

The production conditions, heating oxidation conditions, test results, and the like of the carbon membrane are shown in Tables 1 and 2. In the Tables, the mass of the surface carbon membrane layer 13a of (mass of the surface carbon membrane layer/mass of the entire carbon membrane) in the carbon membrane 11 after carbonization (after thermal decomposition of the carbon-containing layer in an oxygen inert atmosphere and before heating oxidation treatment) and (mass of the surface carbon membrane layer/mass of the entire carbon membrane) in the carbon membrane 11 after the heating oxidation treatment was obtained from the product of thickness obtained by observation of a cross section and bulk density of the carbon membrane, and the mass of the entire carbon membrane was obtained from the difference between the mass of the monolith-shaped substrate 1a having the carbon membrane 11 formed thereon after the carbonization and after the heating oxidation treatment and the mass of the monolith-shaped substrate 1a before forming the carbon membrane 11. Incidentally, the mass of the entire carbon membrane is the mass of the surface carbon membrane layer+ the mass of the composite layer. As the bulk density of the carbon membrane 11, a measurement value of a self-contained carbon membrane produced without using a porous substrate was employed. In addition, the alcohol concentration of an equilibrium vapor of each system was described with referring to Non-patent Document 4 (Hidetoshi Kita et. al, Chem. Commun., 1997, 45.) or was calculated with referring to Non-patent Document 5 (Shuuzou Ooe "Properties Estimation Methods", p. 69, p. 102 to 128, Data Book Publishers (2002)).

TABLE 1

| | | Example 1 | Example 2 | Example 3 | Example 4 | Example 5 | Example 6 | Example 7 | Example 8 |
|---|---|---|---|---|---|---|---|---|---|
| Membrane | Precursor | Phenol resin | Phenol resin | Phenol resin | Phenol resin | Phenol resin | Phenol resin | Phenol resin | Phenol resin |
| | Precursor solution concentration | 5 mass % | 5 mass % | 5 mass % | 5 mass % | 5 mass % | 5 mass % | 5 mass % | 5 mass % |
| | Dip step repetition number | 5 times | 5 times | 5 times | 5 times | 5 times | 5 times | 5 times | 5 times |
| | Mass of surface carbon membrane layer (g)/mass of entire carbon membrane (g) in carbon membrane after carbonization | No surface carbon membrane layer | No surface carbon membrane layer | No surface carbon membrane layer | No surface carbon membrane layer | No surface carbon membrane layer | No surface carbon membrane layer | No surface carbon membrane layer | No surface carbon membrane layer |
| Heating oxidation treatment | Atmosphere | Air | Air | Air | Air | Air | Air | Air | Air |
| | A | 12.3 | 9 | 32 | 6.3 | 12.3 | 12.3 | 12.3 | 12.3 |
| | Temperature | 350° C. | 300° C. | 400° C. | 250° C. | 350° C. | 350° C. | 350° C. | 350° C. |
| | Time | 1 h | 1 h | 2 h | 1 h | 1 h | 1 h | 1 h | 1 h |
| | Flow rate | 1.4 cm/min. | 1.4 cm/min. | 1.4 cm/min. | 1.4 cm/min. | 0.5 cm/min. | 0.25 cm/min. | 1.4 cm/min. | 1.4 cm/min. |
| | Mass of surface carbon membrane layer (g)/mass of entire carbon membrane (g) in carbon membrane after heating oxidation treatment | No surface carbon membrane layer | No surface carbon membrane layer | No surface carbon membrane layer | No surface carbon membrane layer | No surface carbon membrane layer | No surface carbon membrane layer | No surface carbon membrane layer | No surface carbon membrane layer |
| Test results | Supply liquid component | Component 1 | Ethanol | Ethanol | Ethanol | Ethanol | Ethanol | Ethanol | Methanol | Methanol |
| | | Component 2 | n-octane | n-octane | n-octane | n-octane | n-octane | n-octane | Cyclohexane | MTBE |
| | | Component 3 | o-xylene | o-xylene | o-xylene | o-xylene | o-xylene | o-xylene | | |
| | Supply liquid concentration | Component 1 | 33 mass % | 33 mass % | 33 mass % | 33 mass % | 33 mass % | 33 mass % | 50 mass % | 50 mass % |
| | | Component 2 | 33 mass % | 33 mass % | 33 mass % | 33 mass % | 33 mass % | 33 mass % | 50 mass % | 50 mass % |
| | | Component 3 | 33 mass % | 33 mass % | 33 mass % | 33 mass % | 33 mass % | 33 mass % | | |
| | Permeated liquid concentration | Component 1 | 84 mass % | 92 mass % | 81 mass % | 97 mass % | 89 mass % | 95 mass % | 85 mass % | 91 mass % |
| | | Component 2 | 5 mass % | 3 mass % | 6 mass % | 1 mass % | 4 mass % | 2 mass % | 15 mass % | 9 mass % |
| | | Component 3 | 11 mass % | 5 mass % | 13 mass % | 2 mass % | 7 mass % | 3 mass % | | |
| | Alcohol concentration of permeated liquid to equilibrium alcohol concentration | | high | high | high | high | high | high | high | high |
| | α | Component 1/component 2 | 17 | 31 | 14 | 97 | 22 | 48 | 6 | 10 |
| | | Component 1/component 3 | 8 | 18 | 6 | 49 | 13 | 32 | | |
| | Alcohol permeation flux [kg/m²/h] | | 1.8 | 1.0 | 2.5 | 0.8 | 1.5 | 0.8 | 2.6 | 1.6 |

| | | Example 9 | Example 10 | Example 11 | Example 12 | Example 13 | Example 14 | Example 15 |
|---|---|---|---|---|---|---|---|---|
| Membrane | Precursor | Phenol resin | Polyimide resin | Phenol resin | Phenol resin | Phenol resin | Phenol resin | Phenol resin |
| | Precursor solution concentration | 5 mass % | 5 mass % | 5 mass % | 7 mass % | 8 mass % | 10 mass % | 15 mass % |
| | Dip step repetition number | 5 times | 5 times | 5 times | 4 times | 4 times | 3 times | 2 times |
| | Mass of surface carbon membrane layer (g)/mass of entire carbon membrane (g) in carbon membrane after carbonization | No surface carbon membrane layer | No surface carbon membrane layer | No surface carbon membrane layer | 0.2 | 0.3 | 0.5 | 0.6 |

TABLE 1-continued

|  |  |  |  |  |  |  |  |  |
|---|---|---|---|---|---|---|---|---|
| Heating oxidation treatment | Atmosphere | Air | Air | $CO_2$ | Air | Air | Air | Air |
|  | A | 12.3 | 12.3 | 12.3 | 12.3 | 12.3 | 12.3 | 12.3 |
|  | Temperature | 350° C. | 350° C. | 350° C. | 350° C. | 350° C. | 350° C. | 350° C. |
|  | Time | 1 h | 1 h | 1 h | 1 h | 1 h | 1 h | 1 h |
|  | Flow rate | 1.4 cm/min. | 1.4 cm/min. | 1.4 cm/min. | 1.4 cm/min. | 1.4 cm/min. | 1.4 cm/min. | 1.4 cm/min. |
|  | Mass of surface carbon membrane layer (g)/mass of entire carbon membrane (g) in carbon membrane after heating oxidation treatment | No surface carbon membrane layer | No surface carbon membrane layer | No surface carbon membrane layer | 0.2 | 0.3 | 0.5 | 0.6 |
| Test results | Supply liquid component | Component 1 | Ethanol | Ethanol | Ethanol | Ethanol | Ethanol | Ethanol | Ethanol |
|  |  | Component 2 | Cyclohexane | n-octane | n-octane | n-octane | n-octane | n-octane | n-octane |
|  |  | Component 3 |  | o-xylene | o-xylene | o-xylene | o-xylene | o-xylene | o-xylene |
|  | Supply liquid concentration | Component 1 | 50 mass % | 33 mass % | 33 mass % | 33 mass % | 33 mass % | 33 mass % | 33 mass % |
|  |  | Component 2 | 50 mass % | 33 mass % | 33 mass % | 33 mass % | 33 mass % | 33 mass % | 33 mass % |
|  |  | Component 3 |  | 33 mass % | 33 mass % | 33 mass % | 33 mass % | 33 mass % | 33 mass % |
|  | Permeated liquid concentration | Component 1 | 74 mass % | 80 mass % | 97 mass % | 83 mass % | 79 mass % | 78 mass % | 72 mass % |
|  |  | Component 2 | 26 mass % | 6 mass % | 1 mass % | 6 mass % | 7 mass % | 7 mass % | 11 mass % |
|  |  | Component 3 |  | 14 mass % | 2 mass % | 11 mass % | 14 mass % | 15 mass % | 17 mass % |
|  | Alcohol concentration of permeated liquid to equilibrium alcohol concentration |  | high | high | high | high | high | high | High |
|  | α | Component 1/component 2 | 3 | 13 | 97 | 14 | 11 | 11 | 7 |
|  |  | Component 1/component 3 |  | 6 | 49 | 8 | 6 | 5 | 4 |
|  | Alcohol permeation flux [kg/m²/h] |  | 1.7 | 1.0 | 0.8 | 1.8 | 1.8 | 1.8 | 1.8 |

*A = (temperature ° C.)2 × time (h)/10000

TABLE 2

|  |  |  | Comp. Ex. 1 | Comp. Ex. 2 | Comp. Ex 3 | Comp. Ex. 4 | Comp. Ex. 5 | Comp. Ex. 6 | Comp. Ex. 7 |
|---|---|---|---|---|---|---|---|---|---|
| Membrane | Precursor |  | Phenol resin | Phenol resin | Phenol resin | Phenol resin | Phenol resin | Phenol resin | Polyimide resin |
|  | Precursor solution concentration |  | 5 mass % | 5 mass % | 5 mass % | 5 mass % | 5 mass % | 5 mass % | 5 mass % |
|  | Dip step repetition number |  | 5 times | 5 times | 5 times | 5 times | 5 times | 5 times | 5 times |
|  | Mass of surface carbon membrane layer (g)/mass of entire carbon membrane (g) in carbon membrane after carbonization |  | No surface carbon membrane layer | No surface carbon membrane layer | No surface carbon membrane layer | No surface carbon membrane layer | No surface carbon membrane layer | No surface carbon membrane layer | No surface carbon membrane layer |
| Heating oxidation treatment | Atmosphere |  | — | $N_2$ | Air | — | — | — | — |
|  | A |  | — | 12.3 | 40.5 | — | — | — | — |
|  | Temperature |  | — | 350° C. | 450° C. | — | — | — | — |
|  | Time |  | — | 1 h | 2 h | — | — | — | — |
|  | Flow rate |  | — | 1.4 cm/min. | 1.4 cm/min. | — | — | — | — |
| Test results | Supply liquid component | Component 1 | Ethanol | Ethanol | Ethanol | Methanol | Methanol | Ethanol | Ethanol |
|  |  | Component 2 | n-octane | n-octane | n-octane | Cyclohexane | MTBE | Cyclohexane | n-octane |
|  |  | Component 3 | o-xylene | o-xylene | o-xylene |  |  |  | o-xylene |
|  | Supply liquid concentration | Component 1 | 33 mass % | 33 mass % | 33 mass % | 50 mass % | 50 mass % | 50 mass % | 33 mass % |
|  |  | Component 2 | 33 mass % | 33 mass % | 33 mass % | 50 mass % | 50 mass % | 50 mass % | 33 mass % |
|  |  | Component 3 | 33 mass % | 33 mass % | 33 mass % |  |  |  | 33 mass % |
|  | Permeated liquid concentration | Component 1 | 97 mass % | 97 mass % | 33 mass % | 95 mass % | 97 mass % | 95 mass % | 93 mass % |
|  |  | Component 2 | 1 mass % | 1 mass % | 33 mass % | 5 mass % | 3 mass % | 5 mass % | 2 mass % |
|  |  | Component 3 | 2 mass % | 2 mass % | 33 mass % |  |  |  | 5 mass % |
|  | Alcohol concentration of permeated liquid to equilibrium alcohol concentration |  | high | high | Low | high | high | high | high |
|  | α | Component 1/component 2 | 97 | 97 | 1 | 19 | 32 | 19 | 47 |
|  |  | Component 1/component 3 | 49 | 49 | 1 |  |  |  | 19 |
|  | Alcohol permeation flux [kg/m²/h] |  | 0.7 | 0.7 | Too high to measure | 0.8 | 0.5 | 0.6 | 0.3 |

*A = (temperature ° C.)2 × time (h)/10000

(1) Confirmation of Heating Oxidation Treatment Effect

Example 1, Comparative Example 1

In a carbon membrane not subjected to the heating oxidation treatment (Comparative Example 1), the ethanol concentration of the permeated liquid exceeded the vapor composition in gas-liquid equilibrium (ethanol of about 70 mass %), and it is assumed that ethanol was separated. On the other hand, in a carbon membrane subjected to the heating oxidation treatment (Example 1), the permeation flux of ethanol was raised to about 2.6 times in comparison with the carbon membrane not subjected to the heating oxidation treatment while separating ethanol (Comparative Example 1). Though the ethanol concentration of the permeated liquid is decreased in Example 1 in comparison with Comparative Example 1, it is sufficiently higher than the ethanol concentration in gas-liquid equilibrium (about 70 mass %), and the separability is regarded as sufficiently been maintained. That is, by the heating oxidation treatment, permeability of the carbon membrane was raised while maintaining separability. Example 1 has high permeability in comparison with that of Comparative Example 1 and can separate a larger amount of ethanol at the same membrane area. Therefore, according to Example 1, practical merits such as compactification and improvement in efficiency of the separator are provided. Incidentally, in Example 1, the permeation flux of the ethanol having a molecular diameter of 0.43 nm (Non-patent Document 6 (Fluid Phase Equilibr., 99, 1994, 1)) was $4 \times 10^{-7}$ mol/m$^2 \cdot$s$\cdot$Pa. This value was remarkably large in comparison with the gas permeation rate of about $1 \times 10^{-9}$ mol/m$^2 \cdot$s$\cdot$Pa in a molecular diameter of 0.43 nm analogized from the relation between the molecular diameter and the permeation rate of the gas at the carbon membrane subjected to a heating oxidation treatment (FIG. 3) in Non-patent Document 3.

(2) Heating Oxidation Atmosphere

Examples 1, 11, Comparative Examples 1, 2

In the cases that the oxidizing gas was air (Example 1) and $CO_2$ (Example 11), the ethanol permeation flux was raised to about 2.6 times and 1.1 times, respectively, in comparison with the carbon membrane not subjected to the heating oxidation treatment (Comparative Example 1). On the other hand, in the case that the oxidizing gas was $N_2$ (Comparative Example 2), the permeation flux of the ethanol and the composition of the permeated liquid were about the same as those of the carbon membrane not subjected to the heating oxidation treatment (Comparative Example 1).

(3) Effect of Heating Oxidation Temperature and Time

Examples 2, 3, 4, Comparative Example 1, 3

In the cases of Example 2 (temperature of 300° C., time of 1 hour, and A=9), Example 3 (temperature of 400° C., time of 2 hours, and A=32), and Example 4 (temperature of 250° C., time of 1 hour, A=6.3), the ethanol permeation flux was raised to about 1.4 times, 3.6 times, and 1.1 times, respectively, in comparison with the carbon membrane not subjected to the heating oxidation treatment (Comparative Example 1). On the other hand, in the case of Comparative Example 3 (temperature of 450° C., time of 2 hours, A=40.5), ethanol was not separated. In Comparative Example 3, it is assumed that the carbon membrane disappeared by excessive oxidation by an excessive treatment because time was too long with respect to temperature.

(4) Ratio (R) of Oxidizing Gas Supply Flow Rate to Membrane Area

Examples 5 and 6, Comparative Example 1

In the cases of Example 5 (ratio of the oxidizing gas supply flow rate to the area of the membrane subjected to heating oxidation (R)=0.5 cm/min.) and Example 6 (R=0.25 cm/min.), ethanol permeation flux was raised to about 2 times and 1.1 times, respectively, in comparison with a carbon membrane (Comparative Example 1) not subjected to a heating oxidation treatment.

Incidentally, in any of Examples 1 to 6 of (1) to (4), the component concentration of the permeated liquid was ethanol>o-xylene>n-octane. On the other hand, the molecular diameters of these three components were 0.43 nm for ethanol, 0.68 nm for o-xylene (Non-patent Document 7 (Handbook of molecular sieves, Van Nostrand Reinhold, New York, 1992)), and 0.43 nm for n-octane (Non-patent Document 8 (Ind. Eng. Chem. Res., 36, 1997, 137-143)), and the order of the permeated components did not coincide with the size of the molecular diameters. The selective permeation of ethanol is due to easy diffusion of pores because of the small particle diameter and a synergistic effect of an adsorption effect. On the other hand, the reason why the o-xylene having a large molecular diameter with respect to n-octane having a small molecular diameter was selectively permeated is presumed that the former had a high adsorption effect in comparison with the latter.

(5) Other Liquid Mixtures

Example 7 to 9, Comparative Example 4 to 6

Also, regarding each of the liquid mixtures of methanol and cyclohexane (Example 7, Comparative Example 4), methanol and methyl tert-butyl ether (MTBE) (Example 8, Comparative Example 5), and ethanol and cyclohexane (Example 9, Comparative Example 6), a carbon membrane subjected to a heating oxidation treatment exhibited high methanol or ethanol permeation flux in comparison with a carbon membrane not subjected to a heating oxidation treatment while separating methanol or ethanol.

(6) Other Precursors

Example 10, Comparative Example 7

Also, in the case of using polyimide resin as a precursor of the carbon membrane, by performing a heating oxidation treatment, the ethanol permeation flux was raised to 3 times that of the carbon membrane not subjected to the heating oxidation treatment.

(7) Ratio of Surface Carbon Membrane Layer of Carbon Membrane Before Heating Oxidation Treatment Examples 1, 12, 13, 14, 15, Comparative Example 1

Regardless of the difference in (the mass of the surface carbon membrane layer/the mass of entire carbon membrane) after carbonization, any of the carbon membranes subjected to the heating oxidation treatment (Example 1, 12, 13, 14, 15) had high ethanol permeation flux in comparison with the carbon membranes not subjected to the heating oxidation treatment (Comparative Example 1). Though each of Examples 12, 13, 14, and 15 had low ethanol concentration of the permeated liquid in comparison with Example 1, it was higher than the ethanol concentration of 70% in the gas-liquid equilibrium, and the separation effect by the membrane was confirmed. That is, Examples 12, 13, 14, and 15 showed the ethanol separation performance with high ethanol permeation flux. Example 1, where the surface carbon membrane layer 13a was not observed by a scanning electronic microscope, had high ethanol concentration of the permeated liquid and high methanol selectivity in comparison with Examples 12, 13, 14, and 15, where the mass of the surface carbon membrane layer/the mass of entire carbon membrane was 0.2, 0.3, 0.5, and 0.6, respectively. Therefore, it was found out that, without the surface carbon membrane layer 13a, a separation membrane having higher performance can be obtained. Incidentally, the mass of the surface carbon membrane layer/the mass of entire carbon membrane of the carbon membrane subjected to the heating oxidation treatment was the same as that of the carbon membrane before being subjected to the heating oxidation treatment.

It is presumed that the reason why the alcohol permeability of the carbon membrane was improved by the method described in the present application is because the pores became large as a possibility through the reason cannot be determined. However, generally, permeability and separability have a trade-off relation, and therefore permeability increases when the pores become larger whereas separability tends to fall to a large extent. In contrast, according to the carbon membrane produced by the method described in the present application, it was possible to improve permeability with maintaining separability in separation of alcohol from a liquid mixture. It is presumed that this is because separability was not impaired to a large extent even in large pores because the surfaces of the pores of the carbon membrane have high affinity for alcohol and high adsorption effect. From the aforementioned reason, it is presumed that the carbon membrane obtained by the method described in the present application exhibited specifically high alcohol separability and permeability in the separation of alcohol from the liquid mixture.

INDUSTRIAL APPLICABILITY

A carbon membrane produced by a production method of the present invention can be used as a carbon membrane for liquid separation.

DESCRIPTION OF REFERENCE NUMERALS

1: porous substrate, 1a: monolith-shaped substrate, 2: through-hole (linear through-hole), 3: side face, 4: end face, 5: inner wall face, 11: carbon membrane (separation membrane), 11a: membrane supply side, 11b: membrane permeation side, 12: seal portion, 13a: surface carbon membrane layer, 13b: composite layer, 31: raw material side space, 32: permeation side space, 33: o-ring, 35: raw material tank, 36: circulation pump, 37: SUS module, 37a: supply liquid introduction port, 37b: supply liquid discharge port, 37c: permeated vapor collection port, 38: cooling trap, 39: vacuum pump, 51: open portion, 60: longitudinal direction, 70: ceramic tube, 71: heating furnace, 72: SUS tube, 100: separation membrane-provided body, 101: separator

The invention claimed is:

1. A method for producing a carbon membrane, the method comprising thermally decomposing a carbon-containing layer as a precursor in an oxygen inert atmosphere to obtain a carbon membrane and then subjecting the carbon membrane to a heating oxidation treatment in a gas mixture containing oxidizing gas to obtain the carbon membrane which selectively separates alcohols having 2 or less carbon atoms from a liquid mixture of the alcohols having 2 or less carbon atoms and organic compounds having 6 to 9 carbon atoms.

2. The method for producing a carbon membrane according to claim 1, wherein the carbon membrane is subjected to the heating oxidation treatment while sending the gas mixture so that (temperature ° C.)$^2$×hour (h)/10000, which shows a relation between temperature of the gas mixture and time for sending the gas mixture is within the range from 9 to 32.

3. The method for producing a carbon membrane according to claim 1, wherein the carbon membrane is subjected to the heating oxidation treatment while sending the gas mixture so that the ratio of a flow rate of the gas mixture to an area of the carbon membrane is 0.5 cm/min. or more.

4. The method for producing a carbon membrane according to claim 1, wherein the oxidizing gas is oxygen.

5. The method for producing a carbon membrane according to claim 1, wherein the carbon-containing layer as a precursor is a resin layer.

6. The method for producing a carbon membrane according to claim 5, wherein the resin forming the resin layer is at least one kind selected from the group consisting of polyimide based resins and phenol based resins.

7. The method for producing a carbon membrane according to claim 1, wherein the carbon-containing layer is formed on a porous ceramic substrate.

8. The method for producing a carbon membrane according to claim 7, further including forming the carbon membrane after thermal decomposition of the carbon-containing layer in the oxygen inert atmosphere and before the heating oxidation treatment
   so that carbon membrane has at least a composite layer formed in the porous ceramic substrate and
   wherein the mass of the surface carbon membrane layer/ (mass of the surface carbon layer+mass of the composite layer) is 0.5 or less in a relation between the composite layer and the surface carbon membrane layer of the carbon membrane formed and exposed on a surface of the porous ceramic substrate.

9. The method for manufacturing a carbon membrane according to claim 8, wherein the carbon membrane is formed so that the carbon membrane has only a composite layer without having the surface carbon membrane layer after thermal decomposition of the carbon-containing layer in the oxygen inert atmosphere and before the heating oxidation treatment.

10. A carbon membrane produced by the method according to claim 1, wherein the carbon membrane is formed on a porous ceramic substrate and has a composite layer formed in the porous ceramic substrate, and
   the mass of the surface carbon membrane layer/(mass of the surface carbon layer+mass of the composite layer) is 0.5 or less in the relation between the composite layer and the surface carbon membrane layer of the carbon membrane formed and exposed on a surface of the porous ceramic substrate.

11. The carbon membrane according to claim 10, wherein the carbon membrane is formed on the porous ceramic substrate and has only a composite layer formed in the porous ceramic substrate without being exposed on the surface of the porous ceramic substrate.

12. A separator for a liquid mixture comprising a carbon membrane according to claim 10.

* * * * *